US010098590B2

(12) United States Patent
DeFreitas et al.

(10) Patent No.: US 10,098,590 B2
(45) Date of Patent: *Oct. 16, 2018

(54) TABLE FOR PERFORMING MEDICAL PROCEDURES

(71) Applicant: Hologic, Inc., Marlborough, MA (US)

(72) Inventors: Kenneth F. DeFreitas, Patterson, NY (US); Ian Shaw, Yorktown Heights, NY (US); Kathy Pickett, Uncasville, CT (US); Aaron Fand, Bethel, CT (US); Agnes Mercurio, Longpond, PA (US); Linda Volpe, Narragansett, RI (US); Kelly Farmer, Powhatan, VA (US); Darrin Manke, North Andover, MA (US); Erin-Anne A. Lemieux, Milford, NH (US); Christopher Paul Loughnane, Nashua, NH (US); Christopher Labak, Brookline, NH (US)

(73) Assignee: HOLOGIC INC., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/585,140

(22) Filed: May 2, 2017

(65) Prior Publication Data
US 2017/0231575 A1 Aug. 17, 2017

Related U.S. Application Data

(63) Continuation of application No. 13/985,313, filed as application No. PCT/US2011/061186 on Nov. 17, 2011, now Pat. No. 9,649,068.
(Continued)

(51) Int. Cl.
A61B 6/04 (2006.01)
A61B 5/055 (2006.01)
(Continued)

(52) U.S. Cl.
CPC .............. *A61B 5/708* (2013.01); *A61B 5/702* (2013.01); *A61B 5/704* (2013.01); *A61B 6/0435* (2013.01);
(Continued)

(58) Field of Classification Search
CPC ........ A61G 7/015; A61G 7/018; A61G 7/012; A61G 13/06; A61G 13/08; A61G 13/122;
(Continued)

(56) References Cited

U.S. PATENT DOCUMENTS 1,626,091 A 4/1927 Macklin
2,258,782 A 10/1941 McKean
(Continued)

FOREIGN PATENT DOCUMENTS

JP 1994510930 A 12/1994
JP 2006015129 A 1/2006
(Continued)

OTHER PUBLICATIONS

Office Action dated Aug. 25, 2015, in European Patent Application No. 11842380, the corresponding European patent application to the present application.
(Continued)

Primary Examiner — Robert G Santos
(74) Attorney, Agent, or Firm — Kriegsman & Kriegsman

(57) ABSTRACT

The table for performing breast biopsies is characterized by features that enhance patient comfort and facilitate performance of the biopsy. An opening in the table allowing the breast to extend below the table top is formed in a removable insert. An area of the insert includes padding. An alternate insert, having a different diameter opening may be selected based on patient breast size. Another insert having an asymmetrical opening may accommodate the patient's arm when it is desirable to position both the arm and breast of the
(Continued)

patient below the table top. The table top is contoured such that symmetrical distal end sections are elevated relative to a central section to support the patient in multiple positions. A removable pad may be placed over the insert. An end portion for padding the hip of the patient is thicker than an end portion for padding the head/neck of the patient.

24 Claims, 8 Drawing Sheets

Related U.S. Application Data

(60) Provisional application No. 61/415,022, filed on Nov. 18, 2010.

(51) Int. Cl.
    *A61G 13/12*     (2006.01)
    *A61B 5/00*     (2006.01)
    *A61B 10/00*     (2006.01)
    *A61B 10/02*     (2006.01)
    *A61B 6/00*     (2006.01)
    *A61G 13/00*     (2006.01)

(52) U.S. Cl.
    CPC .......... *A61B 6/502* (2013.01); *A61B 10/0041* (2013.01); *A61B 10/0233* (2013.01); *A61G 13/0018* (2013.01); *A61G 13/122* (2013.01); *A61G 13/1235* (2013.01); *A61G 13/1245* (2013.01); *A61G 13/1285* (2013.01); *A61B 5/0555* (2013.01); *A61G 2200/12* (2013.01); *A61G 2200/325* (2013.01); *A61G 2210/50* (2013.01)

(58) Field of Classification Search
    CPC .............. A61G 13/1285; A61B 6/0407; A61B 6/0435; A61B 6/04; A61B 5/0091; A61B 5/0555; A61B 6/502; A61B 5/708
    USPC ... 5/621–624, 610, 613, 601, 600, 632, 731, 5/735; 378/208, 209, 37, 20
    See application file for complete search history.

(56) References Cited

U.S. PATENT DOCUMENTS

| | | |
|---|---|---|
| 2,872,259 A | 2/1959 | Thorpe |
| 4,076,230 A | 2/1978 | Pike |
| 4,596,384 A | 6/1986 | Blosser |
| 5,289,520 A | 2/1994 | Pellegrino et al. |
| 5,400,449 A | 3/1995 | Satto |
| 5,426,685 A | 6/1995 | Pellegrino et al. |
| 5,609,152 A | 3/1997 | Pellegrino et al. |
| 6,480,565 B1 | 11/2002 | Ning |
| 6,739,006 B2 | 5/2004 | Borders et al. |
| 6,754,923 B2 | 6/2004 | Borders et al. |
| 6,883,194 B2 | 4/2005 | Corbeil et al. |
| 6,886,198 B2 | 5/2005 | Marin et al. |
| 6,987,831 B2 | 1/2006 | Ning |
| 7,194,778 B2 | 3/2007 | Riach |
| 7,603,730 B2 | 10/2009 | Zelnik |
| 7,636,967 B1 | 12/2009 | Stokes |
| 7,676,869 B2 | 3/2010 | Zelnik et al. |
| 7,697,660 B2 | 4/2010 | Ning |
| 7,763,864 B2 | 7/2010 | Formenti |
| 7,957,503 B2 | 6/2011 | Kobayashi |
| 8,095,204 B2 | 1/2012 | Smith et al. |
| 8,246,551 B2 | 8/2012 | Miller et al. |
| 8,272,089 B1 | 9/2012 | Stokes |
| 8,458,835 B2 | 6/2013 | Muratalla |
| 8,555,437 B2 | 10/2013 | Gorovitz |
| 8,832,879 B2 | 9/2014 | Rubio |
| 8,914,925 B2 | 12/2014 | Angott |
| 9,649,068 B2 | 5/2017 | DeFreitas et al. |
| 2002/0170115 A1 | 11/2002 | Borders et al. |
| 2002/0170116 A1 | 11/2002 | Borders et al. |
| 2004/0081273 A1 | 4/2004 | Ning |
| 2004/0088791 A1 | 5/2004 | Corbeil et al. |
| 2004/0097811 A1 | 5/2004 | Smith et al. |
| 2004/0111801 A1 | 6/2004 | Marin et al. |
| 2004/0171933 A1 | 9/2004 | Stoller et al. |
| 2005/0055774 A1 | 3/2005 | Marin et al. |
| 2006/0031993 A1 | 2/2006 | Riach |
| 2006/0094950 A1 | 5/2006 | Ning |
| 2006/0112490 A1 | 6/2006 | Chausse |
| 2006/0123546 A1 | 6/2006 | Horton et al. |
| 2007/0033735 A1 | 2/2007 | Formenti |
| 2008/0005840 A1 | 1/2008 | Zelnik |
| 2008/0005841 A1 | 1/2008 | Zelnik et al. |
| 2009/0054772 A1 | 2/2009 | Lin et al. |
| 2009/0064413 A1 | 3/2009 | Sliski et al. |
| 2009/0211584 A1 | 8/2009 | Savich |
| 2010/0069787 A1 | 3/2010 | Miller et al. |
| 2010/0299835 A1 | 12/2010 | Andrews |
| 2011/0010863 A1 | 1/2011 | Rubio |
| 2011/0047705 A1 | 3/2011 | Gorovitz |
| 2011/0083278 A1 | 4/2011 | Muratalla |
| 2013/0198960 A1 | 8/2013 | Angott |
| 2014/0058286 A1 | 2/2014 | DeFreitas et al. |
| 2017/0020474 A1* | 1/2017 | Ning ...................... A61B 6/032 |
| 2017/0231575 A1* | 8/2017 | DeFreitas .............. A61B 5/708 128/845 |

FOREIGN PATENT DOCUMENTS

| | | | |
|---|---|---|---|
| JP | 2006197966 A | 8/2006 | |
| JP | 2008093135 A | 4/2008 | |
| KR | 100150181 A | 10/1998 | |
| KR | 1020070107089 A | 11/2007 | |
| WO | 9311706 A1 | 6/1993 | |

OTHER PUBLICATIONS

Office Action dated May 26, 2015, in Australian Patent Application No. 2011329836, the corresponding Australian patent application to the present application.

Takekawa et al., "Experiences of Using MultiCare Platinum," MEDIX, 47:8-13 (2007).

Office Action dated May 30, 2017, in Japanese Patent Application No. 2016-120221, a corresponding Japanese patent application to the present application.

\* cited by examiner

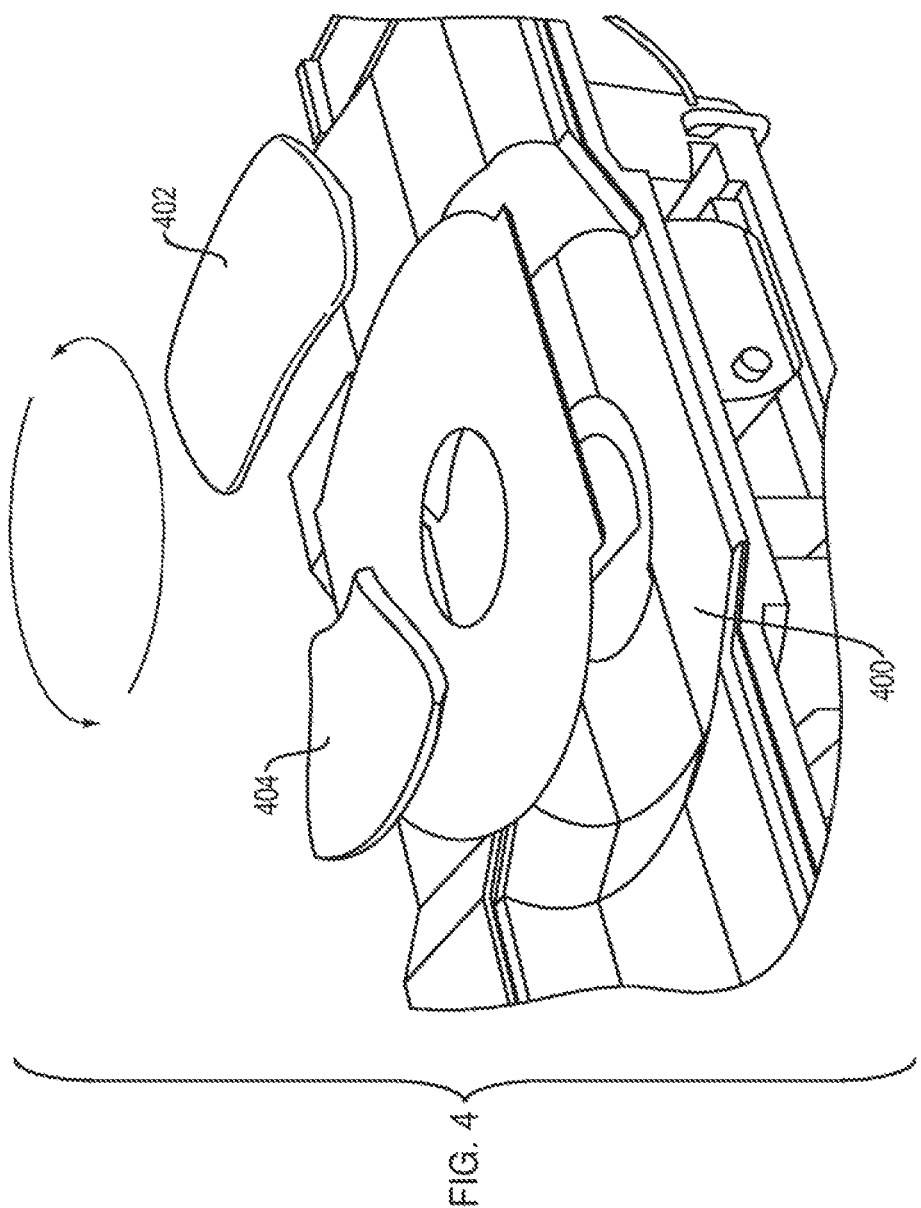

TABLE FOR PERFORMING MEDICAL PROCEDURES

CROSS-REFERENCE TO RELATED APPLICATIONS

The present application is a continuation of U.S. patent application Ser. No. 13/985,313, inventors Kenneth F. DeFreitas et al., filed Aug. 14, 2013, which, in turn, is a 371 of PCT Application No. PCT/US2011/061186, filed Nov. 17, 2011, which, in turn, claims priority of U.S. Provisional Patent Application Ser. No. 61/415,022, filed Nov. 18, 2010, entitled MultiCare RSNA 2009 Maximum Comfort Package Presentation, all of the foregoing being incorporated herein by reference.

BACKGROUND

Screening exams and biopsies are used to detect cancer and other diseases. For example, a mammogram may be obtained to perform a breast cancer screening exam. If an abnormality is detected during the screening exam then a biopsy may be performed. In the case of a breast biopsy the patient's breast is put in compression so that the area of interest associated with the abnormality can be localized. One or more biopsy or "core" tissue samples are then obtained using a biopsy needle. Maintaining position with the breast in compression for the duration of the biopsy can be uncomfortable for the patient.

SUMMARY

In accordance with one aspect or the invention an apparatus comprises: a table top including a rigid platform with an opening for receiving one of a plurality of interchangeable inserts, each insert including a rigid member and a port through which a portion of a patient's body extends during a medical procedure, wherein a first one of the interchangeable inserts is characterized by a different size port than a second one of the interchangeable inserts; and a base including an upright pillar member connected to the table top, the pillar member being positioned to one side of the table top such that an area beneath the table top is available for positioning equipment for performing the medical procedure.

In accordance with another embodiment of the invention a method comprises: configuring a table for a biopsy procedure by selecting one of a plurality of interchangeable inserts, each insert including a rigid member and a port through which a portion of a patient's body extends during a medical procedure, wherein a first one of the interchangeable inserts is characterized by a different size port than a second one of the interchangeable inserts, and mounting a selected insert in a corresponding opening in the table.

The interchangeable inserts and other features enhance patient comfort and facilitate performance of medical procedures such as breast biopsies. For example, an insert having a port size corresponding to the size of the breast of the patient may be selected to provide better support for the patient. An alternative insert having an asymmetrical opening may be selected to accommodate the patient's arm when it is desirable to position both the arm and breast of the patient below the table top. Furthermore, the area of the insert proximate to the perimeter of the port may include flexible material or padding. The table top may be contoured such that symmetrical distal end sections are elevated relative to a central section to support the patient in multiple positions. A removable and rotatable pad may be placed over the insert. An end portion for padding the hip of the patient is thicker than an end portion for padding the head/neck of the patient.

BRIEF DESCRIPTION OF THE DRAWINGS

FIG. 4 illustrates an alternative embodiment of the removable pad.

DETAILED DESCRIPTION

Figure 1:
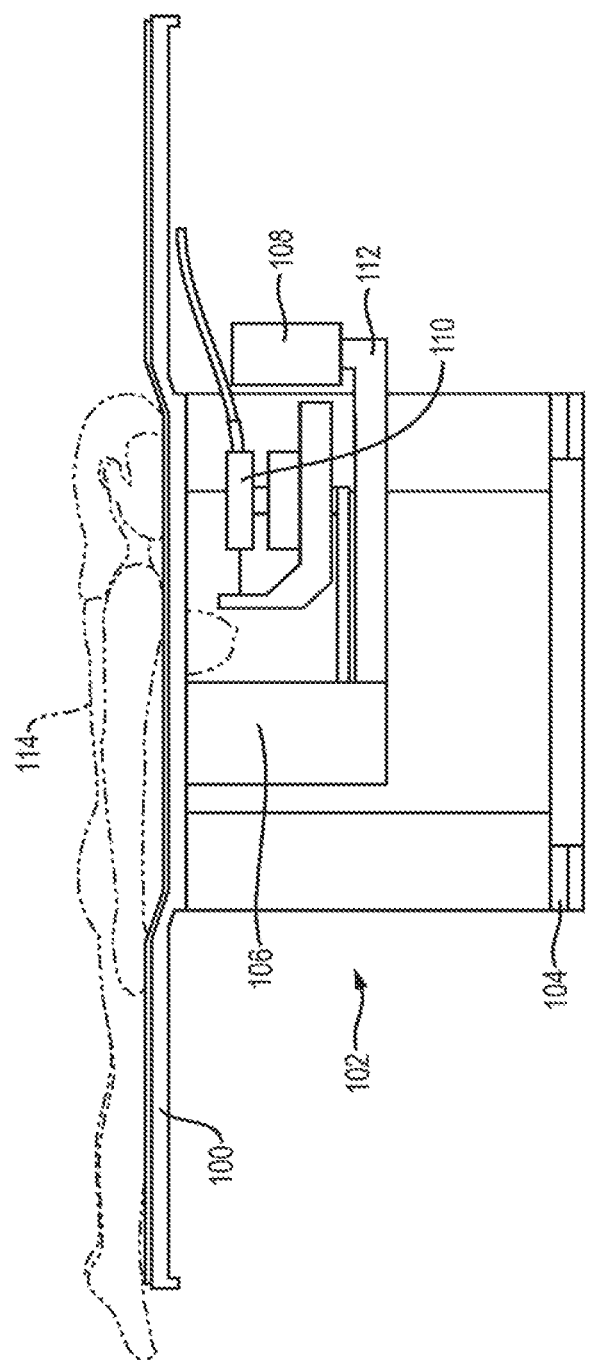
FIGS. 1 and 2 illustrate a table for performing medical procedures such as breast biopsies.
Figure 2:
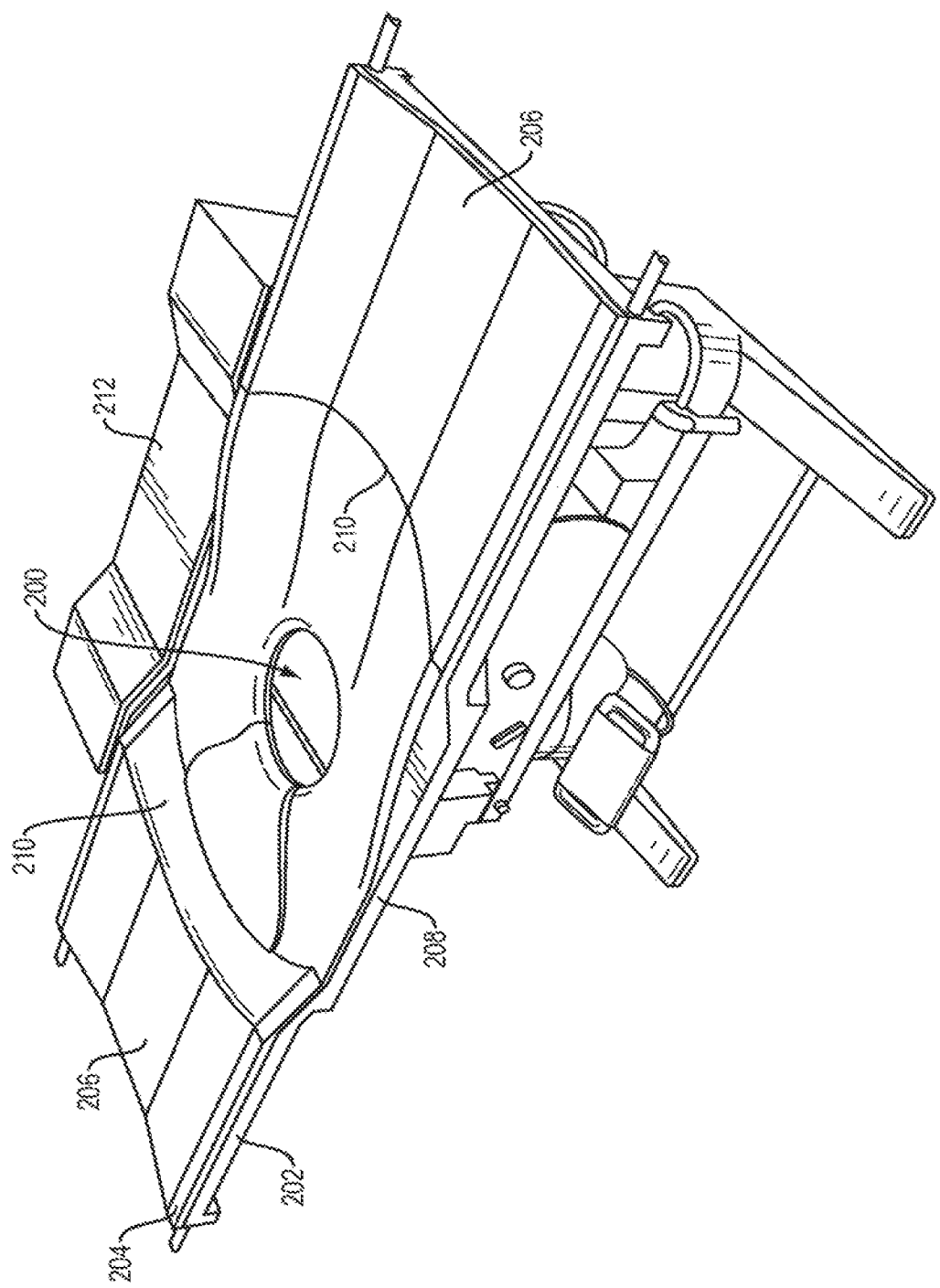
Figure 3A:
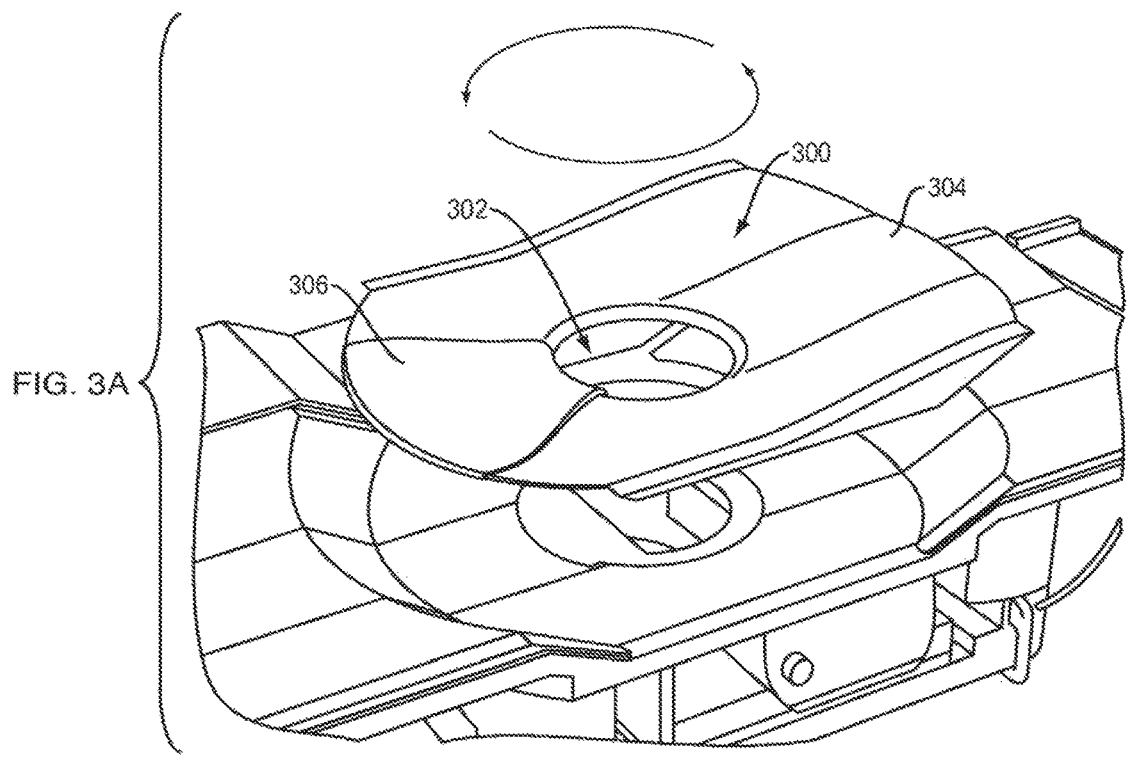
FIGS. 3A and 3B illustrate a removable pad.
Figure 3B:
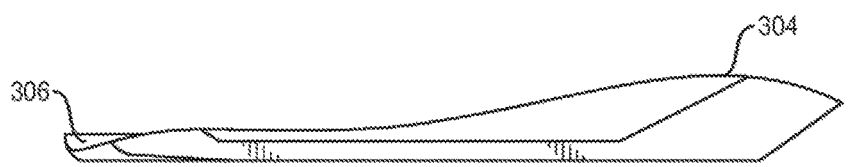

FIGS. 1 and 2 illustrate a table for performing medical procedures such as breast biopsies. The table includes a top 100 which is supported by a base 102. The table top includes a rigid platform 202 at least partially covered with padding 204. AN opening 200 in the table top referred to as a "port" or "aperture" is provided to enable a portion of the body of the patient to extend below the table top. The supporting base includes legs 104 and an upright pillar member 106 via which the base is connected to the table top. The pillar is positioned to one side of the table top such that and area beneath the table top is available for positioning both a portion of the body of the patient and equipment for performing the medical procedure. For example, x-ray imaging equipment 108, a biopsy needle 110 and a needle guidance system may be mounted below the table top. The x-ray imaging equipment includes an x-ray source oriented normal to an x-ray detector. The x-ray source is mounted on a c-arm 112 which pivots such that the x-ray source is movable in an arc to enable generation of stereotactic images. Tubing couples the biopsy needle a vacuum console and filter for capturing excised tissue samples.

A patient 114 undergoing a breast biopsy procedure is oriented in a prone position on the table top such that the breast to be biopsied extends through the port. The breast is then placed in compression and the area of interest associated with the abnormality is localized with the x-ray imaging equipment 108 positioned below the table top. Positioning information from the x-ray imaging equipment is used to configure a needle guidance system and one or more biopsy or "core" tissue samples are then obtained using the biopsy needle. The tissue samples are then imaged to detect indicators such as calcifications.

The table top 100 is contoured such that symmetrical distal end sections 206 are elevated relative to a central section 208. Either of the elevated sections can help support the legs of the patient, thereby allowing 180 degree repositioning of the patient. The central section supports the head, abdomen and hip of the patient. Transitions 210 between the end sections and the central section are angled to provide more comfortable head, abdomen and hip support than an abrupt change of elevation. The top 212 of the pillar member is contoured to match the profile of the table top, e.g., the end sections, central section and transitions. The contours may be formed in either or both of the rigid platform and the padding. Contours help avoid the occurrence of pressure points and unsupported points which tend to cause patient discomfort.

Referring to FIGS. 1, 2, 3A and 3B, the entire table top is covered with padding to enhance the patient comfort. The padding may include one or more foam layers having different characteristics. For example, the padding may include visco-elastic polyurethane "memory" foam and other types of foam. Memory foam is advantageous because it provides comfort but is also relatively thin when compressed under the weight of the patient, which can be helpful because the patient's breast must extend sufficiently below the table. In one embodiment the table top padding includes multiple foam pads. For example, foam pads covering the distal end sections 206 may be permanently attached to the table top. A removable pad 300 may be placed over the central section of the table top. The removable pad includes and opening 302 which is positioned over the port. An end portion 304 for padding the hip of the patient is thicker than an end portion 306 for padding the head/neck of the patient. The ends of the removable pad are angled to match transitions in the permanently attached pads. The removable pad can be rotated 180 degrees when the patient is repositioned by 180 degrees.

Referring now to FIG. 4, in an alternative embodiment the removable pad includes three separate sections. A ring-shaped base section 400 covers the area of the table top between the port and the transitions of the permanently attached pads. The table may be equipped with a kit including multiple base section pads characterized by different thicknesses. The thickness of the pad can be selected for both comfort and optimal positioning of the patient's breast because thicker padding tends to keep the patient elevated relative to thinner padding. A hip pad 402 and a head/neck pad 404 are positioned on top of the base section. The positions of the hip and head/neck pads are swapped when the patient is repositioned by 180 degrees.

Figure 5:
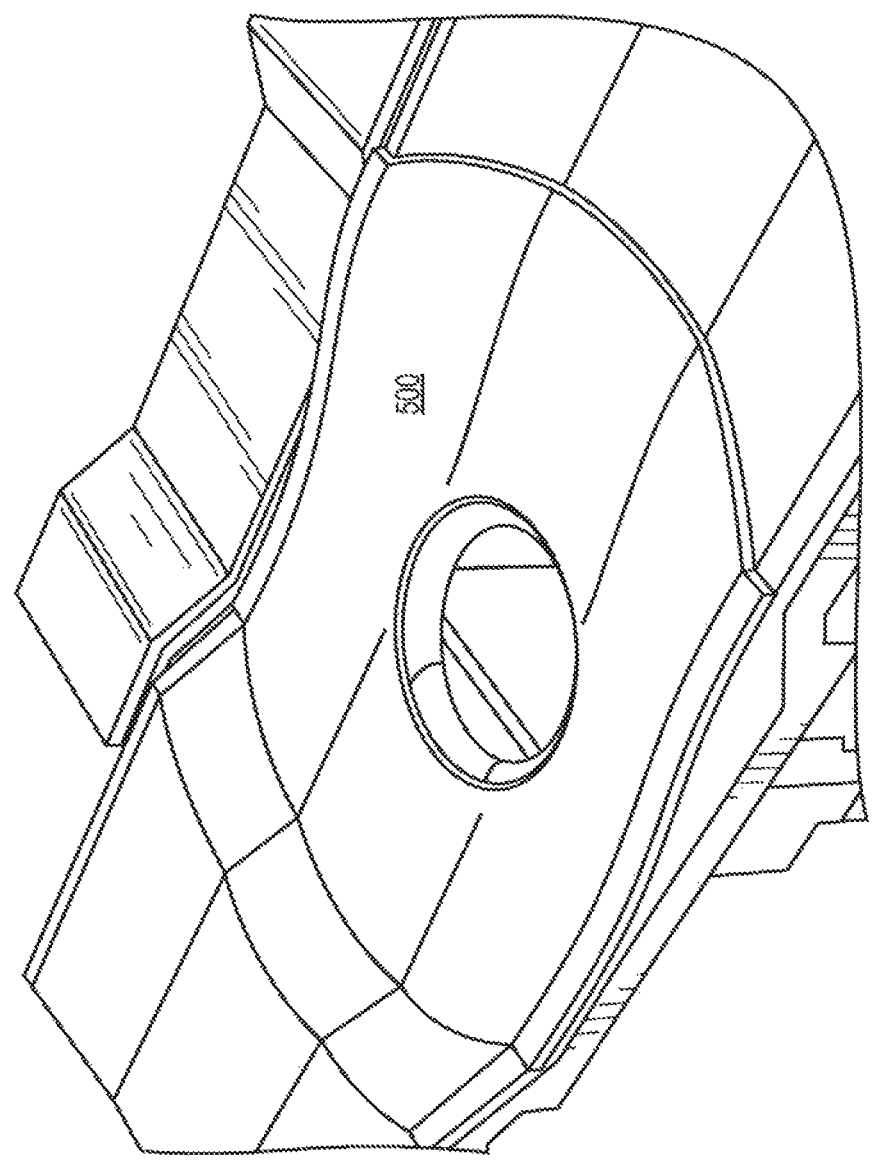
FIG. 5 illustrates an auxiliary pad.

As shown in FIG. 5, an additional layer of padding 500 may be provided to elevate the patient or further enhance comfort. The additional layer of padding is disposed over the removable pad. An opening in the center substantially matches the opening in the removable pad.

Figure 6:
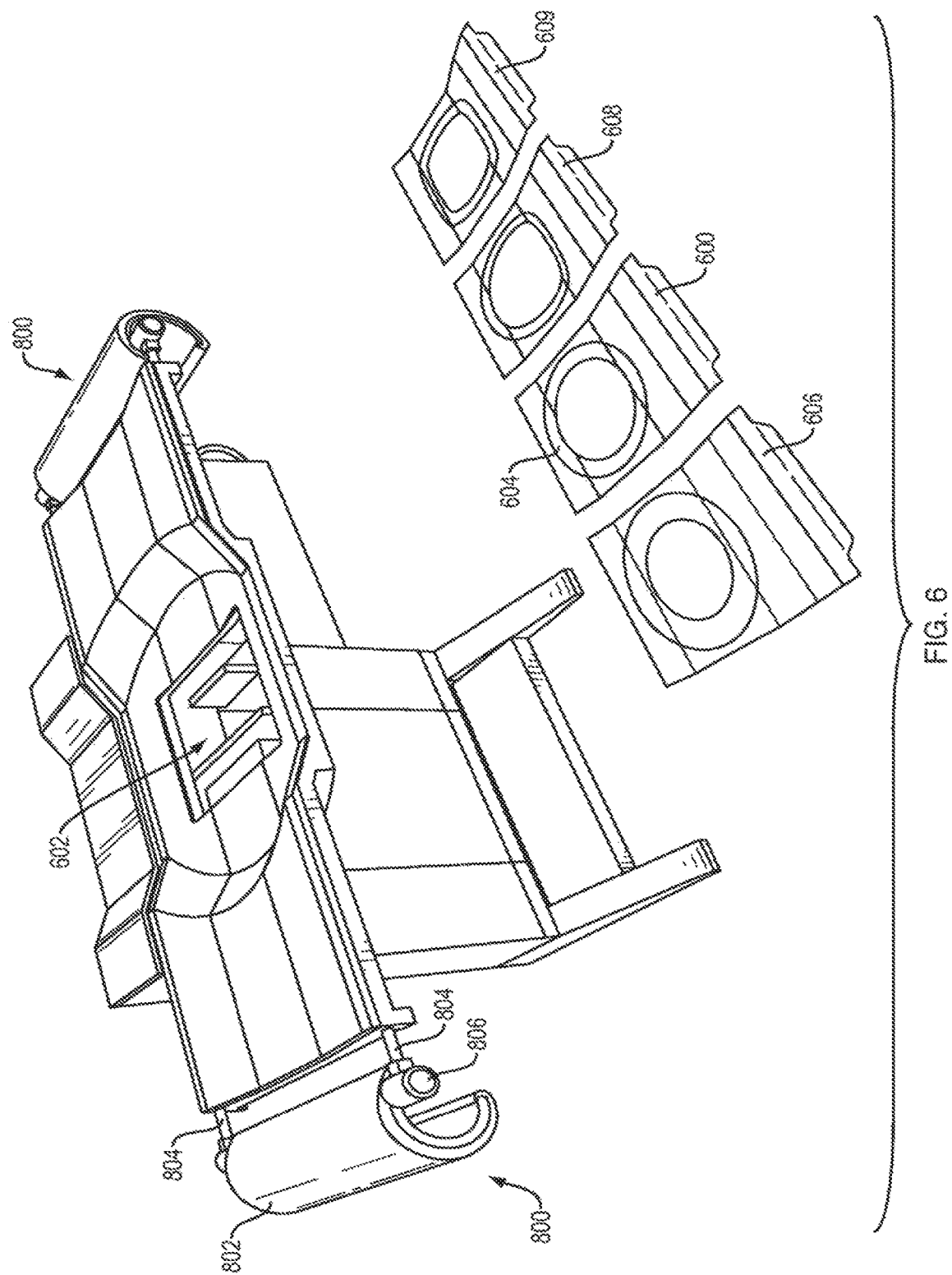
FIG. 6 illustrates a removable insert.

As shown in FIG. 6, the port may be formed in a removable insert 600. The insert includes a rigid sheet member which is formed to fit into a corresponding opening 602 in the table top. A flange or other feature in the table top supports the insert. The insert should be constructed of a material capable of supporting the patient without excessive flex. An area of the insert proximate to the perimeter of the opening includes integral padding 604 and may include a ring of material which is characterized by greater flex than other portions of the insert. An advantage of using removable port inserts is that the size and shape of the insert can be selected to better accommodate the patient. For example, an alternative insert 606 having a larger or smaller diameter opening may be selected based on the size of the patient's breast. Furthermore, an alternative insert 608 having an asymmetrical opening may be selected to accommodate the patient's arm when it is desirable to position both the arm and breast of the patient below the table top. Another alternative is a rectangular insert with rounded corners 609.

Figure 7:
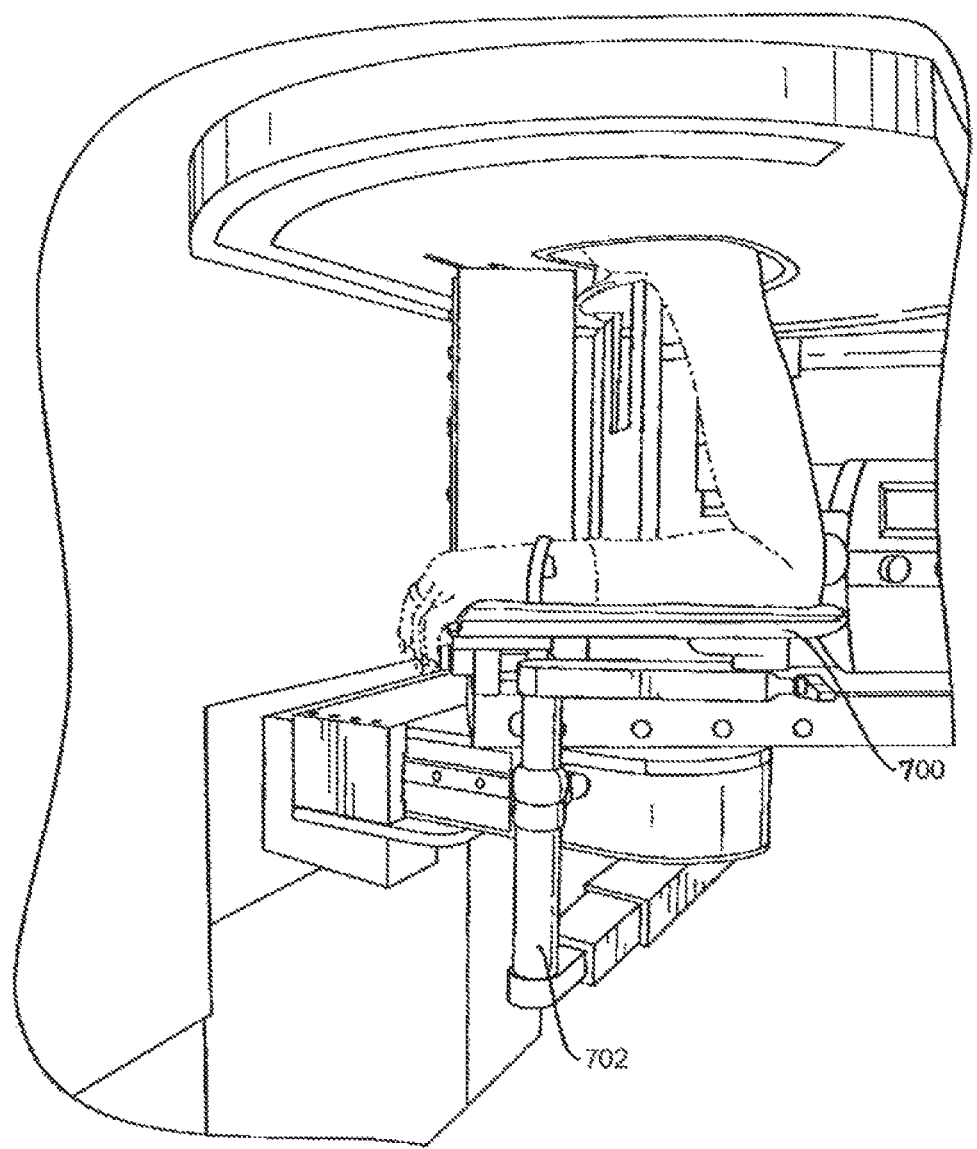
FIG. 7 illustrates an arm support feature.

Referring now to FIG. 7, the table may include a feature for supporting the patient's arm below the table top. The arm support feature includes a horizontal platform 700 which is connected to a shaft member 702. The shaft member is connected to the pillar via an extension arm having a clamp. The shaft member can be moved both rotationally and vertically when the clamp is loosened, thereby allowing three-dimensional adjustment of the position of the horizontal platform.

Figure 8:
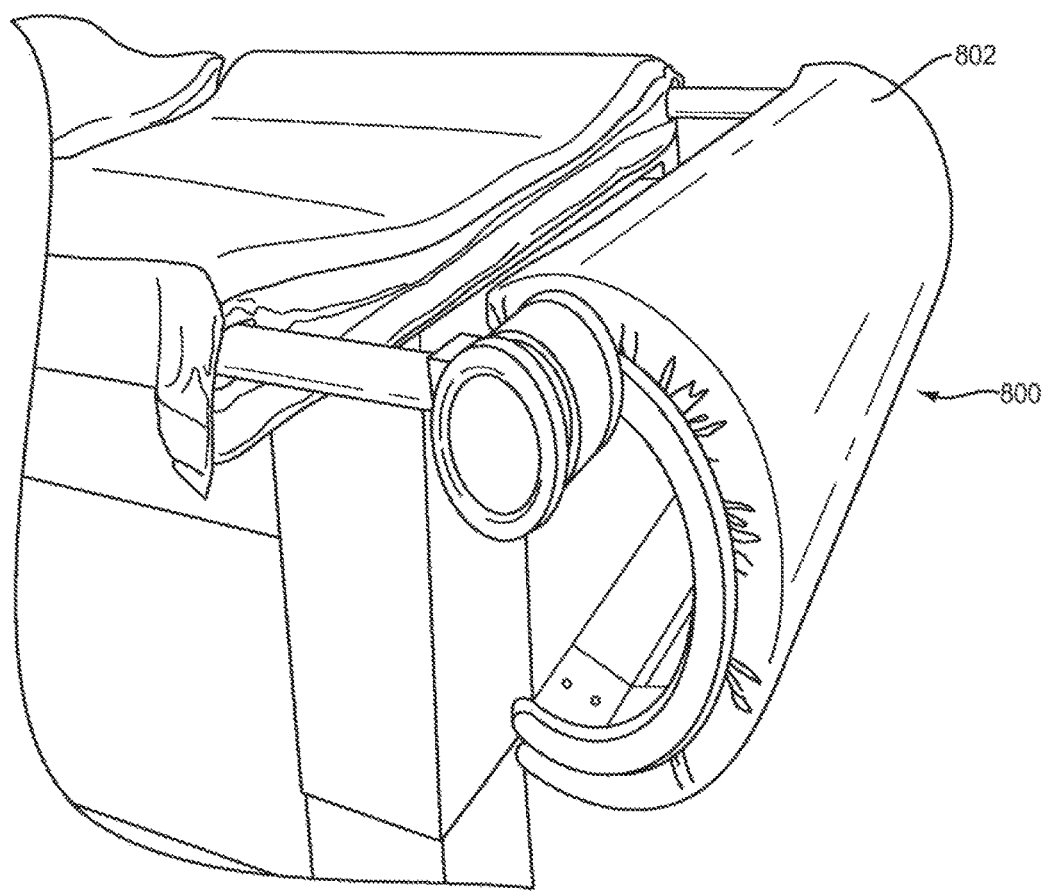
FIG. 8 illustrates an adjustable foot/leg support.

Referring now to FIGS. 6 and 8, extendable foot/leg supports 800 may be provided at both ends of the table top. Each support includes a rounded or arcuate padded member 802 connected to the table via two support shafts 804. The support shafts enable horizontal repositioning. In particular, the support shafts can be moved slidably and secured in position when the foot/leg support is a desired distance from the table top. Typically, patients prefer to have support somewhere between the top of the foot and shin. The foot/leg support also includes a vertical position feature. The support shafts are connected to one end of the padded member via a rotatable joint 806. Consequently, the evaluation of the padded member can be adjusted by rotating the padded member at an axis defined by the rotatable joints. The joint includes a locking feature for securing the padded member in position when a suitable elevation is attained. In one embodiment the locking feature includes a knob with detents which engage projections under spring pressure to enable the padded member to be secured in one of a finite set of positions.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. An apparatus comprising:
   a table top including a rigid platform with an opening;
   a plurality of interchangeable members positionable on the table top, each of the plurality of interchangeable members including a port through which a portion of a patient's body extends during a medical procedure, wherein the port is disposed above and aligns with the opening, wherein a first one of the interchangeable members includes a different size port than a second one of the interchangeable members, wherein when removably mounted on the table top, the plurality of the interchangeable members permit the portion of the patient's body to extend through the ports of the interchangeable members; and
   a base including an upright pillar member connected to the table top, the pillar member being positioned to one side of the table top such that the table top is cantilevered and an area beneath the table top is accessible for positioning equipment for performing the medical procedure.

2. The apparatus of claim 1 wherein one of the interchangeable members includes an asymmetric port dimensioned to receive a breast and an arm.

3. The apparatus of claim 1 wherein one of the interchangeable members includes a rectangular port dimensioned to receive a breast and an arm.

4. The apparatus of claim 1 further comprising a horizontal platform for supporting a patient's arm below the table top, the platform being three dimensionally repositionable.

5. The apparatus of claim 1 wherein the first one of the interchangeable members includes a symmetric port corresponding in size to a breast and wherein the second one of the interchangeable members includes an asymmetric port dimensioned to receive a breast and an arm.

6. The apparatus of claim 1 wherein the table top comprises symmetrical distal end sections and a central section, wherein the table top is contoured such that the symmetrical distal end sections are elevated relative to the central section.

7. The apparatus of claim 1 wherein the table top comprises a central section surrounding the opening, wherein the central section is positioned at a position lower than distal end sections of the table top.

8. The apparatus of claim 1 wherein the plurality of interchangeable members comprises at least two interchangeable pads and wherein the first one of the interchangeable pads includes a first thickness, the second one of the interchangeable pads includes a second thickness, wherein the first thickness is different than the second thickness.

9. The apparatus of claim 8 wherein one of the interchangeable pads further comprises a first end portion, and a second end portion, the first end portion having a greater thickness than the second end portion.

10. The apparatus of claim 1 wherein the plurality of interchangeable members comprises at least two interchangeable inserts, the interchangeable inserts being alternatively positionable over the opening of the table top.

11. The apparatus of claim 1 wherein the plurality of interchangeable members comprises a removable insert and wherein the table top includes a flange that supports the removable insert.

12. The apparatus of claim 1 wherein the plurality of interchangeable members comprises a removable pad and wherein the removable pad is positionable over the opening of the table top.

13. An apparatus comprising:
a table top including a rigid platform with an opening;
a removable pad positionable over the opening in the table top, the removable pad comprising an opening, a first end and a second end, wherein the opening of the removable pad is disposed above and is aligned with the opening of the table top, wherein the first end of the removable pad is thicker than the second end of the removable pad, and wherein the removable pad is positionable over the opening in orientations differing by 180 degrees to permit correspondingly differing orientations of a patient's body on the table top; and
a base including a support member connected to the table top, the support member being positioned such that an area beneath the opening in the table top is accessible for positioning equipment for performing a medical procedure.

14. The apparatus of claim 13 further comprising a plurality of interchangeable inserts, each of the plurality of interchangeable inserts being alternatively positionable over the opening of the table top, each insert including a rigid member and a port through which a portion of the patient's body extends during a medical procedure, wherein a first one of the interchangeable inserts includes a different size port than a second one of the interchangeable inserts.

15. The apparatus of claim 14 wherein the first one of the interchangeable inserts includes a symmetric port corresponding in size to a breast and the second one of the interchangeable inserts includes an asymmetric port dimensioned to receive a breast and an arm.

16. The apparatus of claim 13 wherein the removable pad includes a ring-shaped base section, a hip section, and a head/neck section; the ring-shaped base section, the hip section, and the head/neck section being three separate pieces.

17. The apparatus of claim 13 wherein the removable pad is selected from a plurality of interchangeable removable pads of different thicknesses.

18. The apparatus of claim 13 wherein the table top is symmetric relative to the opening thereof to permit the patient to be positioned in alternative 180 degree positions.

19. The apparatus of claim 13 wherein the table top is contoured such that symmetrical distal end sections are elevated relative to a central section and wherein the symmetrical distal end sections slope down to meet with the central section.

20. An apparatus for use with a mammography system, the system comprising a table top comprising a rigid platform with an opening, and a base including an upright pillar member connected to the table top, the apparatus comprising:
a plurality of interchangeable members positionable on the table top, each of the plurality of interchangeable members including a port through which a portion of a patient's body extends during a medical procedure, wherein the port is disposed above and is aligned with the opening, wherein a first one of the interchangeable members includes a different size port than a second one of the interchangeable members, wherein when removably mounted on the table top, the plurality of the interchangeable members permit the portion of the patient's body to extend through the ports of the interchangeable members and the opening of the table top,
wherein the pillar member is positioned to one side of the table top such that the table top is cantilevered and an area beneath the port of the interchangeable member and the opening of the table top is accessible for positioning equipment for performing the medical procedure.

21. The apparatus of claim 20 wherein the plurality of interchangeable members comprises a plurality of interchangeable inserts, the interchangeable inserts being alternatively positionable over the opening of the table top.

22. The apparatus of claim 20 wherein the plurality of interchangeable members comprises a plurality of interchangeable pads, the interchangeable pads being alternatively positionable over the opening of the table top.

23. The apparatus of claim 20 wherein the plurality of interchangeable members comprises a removable insert, the removable insert being adapted to be supported by a flange in the table top.

24. The apparatus of claim 20 wherein the plurality of interchangeable members comprises a removable pad and wherein the removable pad is positionable over the opening of the table top.

* * * * *